United States Patent
Hohmann et al.

(10) Patent No.: US 9,844,796 B2
(45) Date of Patent: Dec. 19, 2017

(54) PLUNGER AND PLUNGER ASSEMBLY FOR A CARTRIDGE, SYSTEM FOR STORING A SUBSTANCE, AND METHOD OF FILLING AND SEALING A SUBSTANCE IN A DELIVERY SYSTEM

(75) Inventors: Arno Hohmann, Munich (DE); Marc Peuker, Schondorf (DE); Sebastian Guggenmos, Peissenberg (DE); Michael Knee, Peissenberg (DE); Bruce R. Broyles, Oakdale, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1274 days.

(21) Appl. No.: 12/089,920

(22) PCT Filed: Oct. 12, 2006

(86) PCT No.: PCT/US2006/039908
§ 371 (c)(1),
(2), (4) Date: Apr. 11, 2008

(87) PCT Pub. No.: WO2007/047381
PCT Pub. Date: Apr. 26, 2007

(65) Prior Publication Data
US 2008/0230565 A1    Sep. 25, 2008

Related U.S. Application Data

(60) Provisional application No. 60/726,815, filed on Oct. 14, 2005.

(51) Int. Cl.
*B67D 7/60* (2010.01)
*B05C 17/005* (2006.01)
*B05C 17/00* (2006.01)
*A61C 5/62* (2017.01)
*A61C 5/66* (2017.01)

(52) U.S. Cl.
CPC .......... *B05C 17/00576* (2013.01); *A61C 5/62* (2017.02); *A61C 5/66* (2017.02); *B05C 17/003* (2013.01); *B05C 17/00553* (2013.01)

(58) Field of Classification Search
CPC ............ B05C 17/00576; B05C 17/003; B05C 17/00553; A61C 5/66; A61C 5/62
USPC ....................... 222/386, 387, 137, 145.5, 136
See application file for complete search history.

(56) References Cited

U.S. PATENT DOCUMENTS

| 358,477 A | * | 3/1887 | Pitney ...................... E06B 3/44 |
| | | | 49/125 |
| 2,607,341 A | | 8/1952 | Brown .......................... 128/218 |
| 2,752,920 A | * | 7/1956 | Kurkjian .................. A61M 3/00 |
| | | | 222/386 |

(Continued)

FOREIGN PATENT DOCUMENTS

| DE | 42 29 588 | 3/1994 | ............. B65D 83/76 |
| DE | 295 06 800 U | 8/1996 | ........... B05C 17/005 |

(Continued)

*Primary Examiner* — Arthur O Hall
*Assistant Examiner* — Joel Zhou (57) ABSTRACT

The present invention is directed to a plunger, a plunger assembly, and a system for storing a substance or substances, preferably flowable substances, and a method of filling and sealing a substance in a storing system. In particular, the present invention provides for substantially air-free filling and storing of substances in a delivery system.

13 Claims, 11 Drawing Sheets

(56) References Cited

U.S. PATENT DOCUMENTS

| | | | |
|---|---|---|---|
| 3,494,359 A * | 2/1970 | Zackheim | A61M 5/284 222/137 |
| 3,603,310 A | 9/1971 | Mottin et al. | 128/218 |
| 3,674,181 A | 7/1972 | Marks et al. | |
| 3,735,900 A | 5/1973 | Gores | |
| 3,965,898 A | 6/1976 | Cloyd | 128/220 |
| 3,967,759 A | 7/1976 | Baldwin et al. | |
| 4,082,121 A | 4/1978 | Sturm et al. | 141/27 |
| 4,182,238 A | 1/1980 | Mitchell, Sr. et al. | 100/99 |
| 4,235,235 A | 11/1980 | Bekkering | 128/218 |
| 4,310,102 A | 1/1982 | Walter | |
| 4,496,344 A | 1/1985 | Kamstra | |
| 4,599,082 A | 7/1986 | Grimard | |
| 4,613,326 A | 9/1986 | Szwarc | 604/89 |
| 4,689,042 A | 8/1987 | Sarnoff et al. | 604/89 |
| 4,693,706 A * | 9/1987 | Ennis, III | A61M 5/31596 604/220 |
| 4,755,169 A | 7/1988 | Sarnoff et al. | 604/51 |
| 4,951,848 A | 8/1990 | Keller | 222/386 |
| 4,986,443 A | 1/1991 | Saur et al. | 222/1 |
| 5,016,782 A | 5/1991 | Pfanstiel | 222/257 |
| 5,033,650 A | 7/1991 | Colin et al. | |
| 5,178,305 A | 1/1993 | Keller | 222/386 |
| 5,238,003 A | 8/1993 | Baidwan et al. | 128/765 |
| 5,316,186 A | 5/1994 | Prestele | 222/327 |
| 5,400,926 A | 3/1995 | Keller | 222/327 |
| 5,429,603 A * | 7/1995 | Morris | A61M 5/3145 604/87 |
| 5,599,312 A | 2/1997 | Higashikawa | |
| 5,716,338 A | 2/1998 | Hjertman et al. | |
| 5,938,439 A | 8/1999 | Mertins et al. | |
| 6,027,481 A | 2/2000 | Barrelle et al. | |
| 6,102,699 A | 8/2000 | Galehr et al. | 433/90 |
| 6,261,094 B1 | 7/2001 | Dragan | 433/90 |
| 6,544,233 B1 * | 4/2003 | Fukui | A61M 5/31596 604/191 |
| 6,598,766 B1 | 7/2003 | Brugner | 222/326 |
| 6,685,063 B2 | 2/2004 | Brugner | 222/387 |
| 6,698,622 B2 | 3/2004 | Sawhney et al. | |
| 6,740,062 B2 | 5/2004 | Hjertman | |
| 2004/0122359 A1 * | 6/2004 | Wenz | A61M 5/31511 604/82 |
| 2004/0261888 A1 | 12/2004 | Brennan | 141/2 |
| 2008/0203112 A1 | 8/2008 | Peuker | |

FOREIGN PATENT DOCUMENTS

| | | | |
|---|---|---|---|
| DE | 197 20 896 | 12/1997 | F15B 13/042 |
| DE | 298 11 344 U | 10/1999 | B65D 83/76 |
| DE | 101 51 104 | 4/2003 | B65D 81/32 |
| DE | 202 16 632 U | 3/2004 | A61M 5/315 |
| EP | 0004743 | 9/1982 | |
| EP | 0 112 574 | 7/1984 | A61M 5/28 |
| EP | 0 229 820 | 7/1987 | A61M 5/30 |
| EP | 0 313 519 | 4/1989 | B05C 17/00 |
| EP | 0 344 491 | 12/1989 | B65D 83/00 |
| EP | 0 347 546 | 12/1989 | B65D 83/00 |
| EP | 0 463 991 | 1/1992 | B65D 83/00 |
| EP | 0 497 739 | 8/1992 | B05C 17/00 |
| EP | 0 966 331 | 12/1999 | B05C 17/01 |
| EP | 1 308 218 | 5/2003 | B05C 17/01 |
| FR | 2 626 248 | 7/1989 | B65D 47/34 |
| GB | 2 096 299 | 10/1982 | F17C 1/16 |
| JP | 59-134111 | 8/1984 | |
| JP | 6162855 | 4/1986 | |
| JP | 64058674 | 3/1989 | |
| JP | 1-91705 | 6/1989 | |
| JP | H07-075672 | 3/1995 | |
| JP | 9301301 | 11/1997 | |
| JP | 10119298 | 5/1998 | |
| JP | 2005029243 | 2/2005 | |
| WO | WO 89/00536 | 1/1989 | B65D 81/32 |
| WO | WO 90/05096 | 5/1990 | B65D 83/00 |
| WO | WO 91/05731 | 5/1991 | B67D 5/00 |
| WO | WO 93/22200 | 11/1993 | B65B 31/04 |
| WO | WO 95/28337 | 10/1995 | |
| WO | WO 01/94028 | 12/2001 | B05C 17/01 |
| WO | WO 2005/016783 | 2/2005 | B65D 81/32 |
| WO | WO 2006/132932 | 12/2006 | B05C 17/005 |

* cited by examiner

PLUNGER AND PLUNGER ASSEMBLY FOR A CARTRIDGE, SYSTEM FOR STORING A SUBSTANCE, AND METHOD OF FILLING AND SEALING A SUBSTANCE IN A DELIVERY SYSTEM

CROSS REFERENCE TO RELATED APPLICATIONS

This application is a national stage filing under 35 U.S.C. 371 of PCT/US2006/039908 filed Oct. 12, 2006 which claims priority to U.S. Provisional Application No. 60/726, 815, filed Oct. 14, 2005, the disclosure of which is incorporated by reference in their entirety herein.

FIELD OF THE INVENTION

The present invention is directed to a plunger, a plunger assembly, and a system for storing a substance or substances, preferably flowable substances, and a method of filling and sealing a substance in a delivery system. In particular, the present invention provides for substantially air-free filling and storing of substances in a delivery system.

BACKGROUND OF THE INVENTION

A common difficulty encountered during the manufacturing of standard delivery systems is to provide encapsulation of the stored substance without voids or air bubbles. A standard process to avoid trapping air in a storage system or delivery system during assembly of the plunger of the system is to assemble the system under vacuum. However, a total absence of air cannot be achieved, so there will be a small amount of remaining air in the storage or delivery system. Furthermore, the use of a vacuum can also cause evaporation of the ingredients of the substance. The evaporation of ingredients may have a serious impact on the stored substance if the filling volume is very small, such as 1 ml or less, and if precise dosing is important, as with pharmaceutical products.

Another conventional process for filling a delivery system is to do so from the front end of the dispenser, which is the end through which the stored substance is dispensed. The plunger is thereby pushed backwards during filling. However, this process is limited to systems that allow filling from the front end.

U.S. Pat. No. 5,178,305 relates to a dispensing cartridge with a storage cylinder and a dispensing piston whose bottom surface facing the cartridge contents is progressively recessed towards an air evacuation bore. The evacuation bore is sealed by a closure.

WO 01/94028 relates to a ventilation device for a piston for a cartridge, comprising a first piston part which rests sealingly against the cartridge wall and a second piston part, which forms a valve together with the first piston part. Said valve opens when a pressure is exerted on the rear side of the piston so that the air that is trapped between the filling composition and the piston can escape. According to the invention, a filter section is provided in front of the valve, between the two piston parts, as seen from the flow path of the air through the valve. This filter section has at least one narrow channel which forms a penetration barrier for the filling mass and ensures that the valve remains dry and free of dirt.

Further reference is made to EP-A-0 344 491, EP-A-0 463 991, FR-A-2 626 248, EP-A-0 497 739, and U.S. Pat. No. 4,951,848.

SUMMARY OF THE INVENTION

According to a first aspect, the present invention provides a plunger for a cartridge. The plunger has a first end and an opposite second end. The plunger comprises a passageway which extends between the first and second ends. The plunger comprises at least one constriction that is arranged in the passageway between the first end and the second end. The diameter of the constriction is smaller than the smallest diameter of a plug that is movably insertable into the passageway.

The diameter of the constriction is preferably smaller than the diameter of the plug, at least in the area where the constriction seals with the plug. Furthermore, the diameter of the passageway of the plunger is preferably in at least one location other than at the constriction larger than the largest diameter of the plug. This provides that the constriction of the plunger seals with a plug that is movably insertable into the passageway of the plunger. Trapped air in the cartridge can escape through the gap between the wall of the passageway and the inserted plug until the seal is established between the constriction and the plug. It is preferred that the cartridge is then substantially free of air. According to the present invention, substantially free of air is defined as being free of air to the point where any remaining air does not interfere with the purpose or effect of the material being dispensed.

According to a preferred embodiment, the constriction of the plunger forms a sealing lip that forms the seal with the plug. The sealing lip, the plug, or both are preferably deformable. Thus, once the plug is inserted into the passageway and reaches the sealing lip, the plug deflects the sealing lip (or the sealing lip deflects the plug, or each of them deflects), and the sealing lip is biased against the plug.

The present invention also encompasses that the inner surface of the plunger at the first end of the plunger is angled backwardly towards the passageway. In other words, the first end surface of the plunger is inwardly tapered towards the passageway, or progressively recessed towards the passageway. This assists in guiding trapped air along the first end surface to the passageway once the plunger is inserted and moved toward the substance in the cartridge.

According to a preferred embodiment, the backwardly-angled first end surface of the plunger terminates at the constriction. Alternatively, the constriction is set back in the passageway with respect to the backwardly-angled first end surface of the plunger.

According to a second aspect of the present invention, a plunger for a cartridge is provided. The plunger has a first end and an opposite second end, and a passageway that extends between the first and second ends. The passageway comprises a deformable first sealing lip that projects into the passageway.

As described with respect to the first aspect of the present invention, the first end surface of the plunger of the second aspect is preferably angled backwardly towards the passageway, and more preferably terminates in the deformable first sealing lip.

The deformable sealing lip is preferably deformable by a plug that is insertable into the passageway from the second end of the plunger and movable in the passageway. More preferably, the first sealing lip is deformable by the plug towards the first end of the plunger. The deformable first sealing lip and the inserted plug form a seal. Alternatively, the first sealing lip is not deformable but rigid, and the plug is deformable by the rigid lip.

Prior to the insertion of a plug, the surface of the first sealing lip is preferably angled or canted towards the passageway. More preferably, the first sealing lip comprises an edge.

The smallest diameter of the passageway of the plunger of the second aspect is preferably smaller at the first sealing lip than the smallest diameter of the plug.

It is preferred according to the first and second aspect of the present invention that the outer diameter of the plunger increases towards the edge of the plunger at its first end. Thus, the plunger comprises a first part having a substantially constant outer diameter, and a second part having a diameter that increases from the diameter of the first part towards the first end of the plunger. Preferably, the edge at the first end of the plunger is formed as a second sealing lip for sealing against an outside wall, for example of the cartridge.

The plunger of the first or second aspect is preferably cylindrical in shape.

According to a third aspect, the present invention provides a plunger assembly for a cartridge. The plunger assembly comprises a plunger with a first end and an opposite second end, and with a passageway extending between the first and second ends. The plunger assembly further comprises a plug that is insertable into the passageway. The plunger assembly also comprises at least one constriction within the passageway between the first end and the second end of the passageway/plunger. The diameter of the constriction is smaller than the diameter of the plug, at least in the area where the constriction seals with the plug. The constriction preferably forms a sealing lip for forming a seal with the plug. More preferably, the sealing lip is deformable. Alternatively, the sealing lip is not deformable but rigid, and the plug is deformable by the rigid lip It is also preferred at the plunger assembly according to the third aspect of the present invention that the diameter of the passageway in at least one location other than at the constriction is larger than the largest diameter of the plug.

A retention element may be provided for locking the plug with the plunger when being assembled. Preferably, the plug comprises a stepped configuration having a first diameter in the area where the constriction seals with the plug, and a second larger diameter closer to the front end of the plug. Thus, the plug is locked with the plunger against a reverse movement once it is inserted into the passageway in that the constriction abuts against the step. More preferably, the stepped configuration is provided in form of an indented ring into which the constriction lip fits to lock the plug in place. It is further preferred that locking of the plug happens before (e. g. short before) the plug has reached its end position while it is inserted into the passageway so as to provide the possibility to move the plug to its end position and to move it back to the lock position. Alternatively, the passageway includes an indented ring, and the plug includes a protruding ridge for locking the plug with the plunger.

According to a fourth aspect, the present invention relates to a system for storing a substance. The system comprises a container having a compartment for storing the substance, and a plunger according to the present invention. The plunger is displaceable in the container compartment. Furthermore, the system also comprises a plug that is displaceable in the passageway of the plunger. Preferably, the compartment is a generally cylindrical compartment.

As described above, the plunger of the system for storing a substance according to the invention comprises at least one constriction that is arranged in the passageway between the first end and the second end of the plunger. The diameter of the constriction is smaller than the smallest diameter of the plug, at least in the area where the constriction touches the plug. Furthermore, the diameter of the plug is preferably smaller than the diameter of the passageway. More preferably, a space is formed between the wall of the passageway and the plug such that air trapped in the container compartment is allowed to escape through this space, and such that excess substance in the compartment is receivable in this space when the plunger is moved in the compartment. Preferably, excess substance is stored in the space once the plug has reached the first sealing lip of the plunger.

In the system for storing a substance according to the invention, the plunger preferably comprises a first end edge that is formed as a second sealing lip for sealing against an outside wall. Preferably, the second sealing lip abuts against the inner wall of the container compartment.

According to a preferred embodiment of the invention, the plug comprises at its back end a flange. The diameter of the flange is preferably sized to close the space at the second end of the plunger. Thus, the diameter of the flange corresponds to the inner diameter of the plunger passageway at the second end of the plunger.

The container may also comprise a dispensing opening for dispensing the stored substance.

The stored substance is preferably a dental substance, for example, a dental paste or fluid such as a resin modified glass ionomer filling material, composite filling material, modified composite material, etc.

According to a preferred embodiment of the present invention, the container of the system comprises two or more compartments for storing different substances. For each compartment, a plunger according to the invention is preferably provided. The system also comprises further plugs being displaceable in the passageways of the plungers for the additional compartments. In this case, the plugs are preferably connected to each other, for example by a connecting bar. More preferably, the plungers are connected to each other at their second end. It is further preferred that the plungers are connected to each other by a connecting bar that is integrally formed as one piece with the plungers. The plugs may also be integrally formed as one piece with the connecting bar. Preferably, a retention element is provided for locking the plugs with the plunger when being assembled. It is further preferred that locking of the plugs happens before (e.g. shortly before) the plugs have reached their end position while they are inserted into the passageways so as to provide the possibility to move the plugs to their end position and to move them back to the lock position.

According to a fifth aspect of the present invention, a method of filling and sealing a substance in a storing system is provided. A container having a compartment for the substance is provided. The compartment is filled with the substance. A plunger according to the invention is placed into the compartment. The plunger is advanced further towards the substance until the substance passes the first sealing lip of the plunger, wherein air is able to escape into the passageway. The plug is pushed into the passageway of the plunger until the first sealing lip is sealed against the plug.

Preferably, excess substance passing the first sealing lip is received in the space between the wall of the passageway and the plug. The plug and the first sealing lip preferably form a seal against the substance contained in the compartment.

According to a further embodiment the seal is provided as separate part and assembled into the passageway of the plunger. The seal preferably has a triangular cross-sectional shape or a circular cross-sectional shape (O-ring). The passageway of this embodiment preferably (but not necessarily) has a stepped configuration, which means that the passageway has a first diameter towards the front end of the plunger and a second diameter towards the back end of the plunger, wherein the first diameter is smaller then the second diameter. The seal is received in the second diameter and abuts at the step between the first and second diameter, thus being fixed against displacement when the plug is inserted in the passageway. Preferably, the plug comprises a circumferential flange for pressing the seal against the step.

According to another further embodiment the seal is provided at the front end of the plug rather than in the passageway. The seal is preferably of a triangular cross-sectional shape and preferably deformable, thus forming a flexible sealing lip.
Preferably the diameter of the sealing lip is substantially larger than the diameter of the passageway. The plug is preferably pre-assembled with the plunger in a manner that the back end of the plug is located in the passageway of the plunger and the sealing lip is located outside of the passageway. Preferably the sealing lip is located within the inwardly tapered area at the front end of the plunger, wherein the sealing lip does not touch the plunger, providing that the plug does not seal with the plunger at this stage.

According to a further alternative embodiment of the present invention, a method of filling and sealing a substance in a storing system is provided. A container having a compartment for the substance is provided. The compartment is filled with the substance. A plunger assembly according to the second alternative embodiment is placed into the compartment. The plunger assembly is advanced further towards the substance until the substance penetrates into the front end of the passageway of the plunger, wherein air is able to escape between the plug and the passageway. The plug is pulled back towards the back end of the plunger until the sealing lip has moved into the passageway, thus sealing with the plunger. Because of the larger diameter of the sealing lip and because the sealing lip is deformable the sealing lip deflects towards a direction of the substance filled in the compartment when it is moved into the passageway.

The present invention provides various advantages. First, ventilation is provided so that air contained in the compartment can escape while the plunger is inserted so that substantially no air is trapped in the container. Furthermore, a good encapsulation of the material is achieved which is very important with respect to aging of the material. An increased sealing effect is provided by the present invention upon expelling material (when the plunger is pushed forward), because both the first and second seals increase contact force to their respective contact surface upon increase of pressure in the container compartment (upon expelling material). Furthermore, the plunger, the plunger assembly, and the system of the invention are easy to manufacture.

A further advantage of the plunger of the invention is that the system can be filled through the plunger so that the container-plunger assembly can in fact be preassembled. In this case the plunger is placed in the container, and this pre-assembly is placed in the filling machine for filling the material through the passageway of the plunger into the container. After filling, the container-plunger pre-assembly is closed by the plug. Preferably closing is done by the steps of inserting the plug into the passageway completely and moving it back by a short distance so as to relieve the pressure in the container.

A further advantage of the invention over conventional systems is that it can compensate for unequal filling performance during manufacturing, to a considerable extent, because it allows to accommodate a considerable amount of substance in the passageway of the plunger so as to provide that the plunger can be moved to a predefined position when inserted into the compartment while excess substance is displaced into the passageway of the plunger.

The excess substance is encapsulated between the wall of the passageway and the outer surface of the plug when the plug has been inserted into the passageway.

This is furthermore of advantage in combination with a system comprising a container having two or more compartments, because the plungers can be inserted into the container simultaneously to a predefined position while excess substance from all compartments will be displaced into the passageways of the plungers independently from one another.

All described embodiments of the invention may also be used with a delivery system that allows filling from the front end (e. g. filling through the dispensing opening of the delivery system). In this case the plunger may be preassembled in the container. The container fills from the front end towards the back end, wherein the air escapes through the passageway of the plunger. Filling is stopped when substance has passed the sealing lip in the plunger. After filling, the container-plunger pre-assembly is closed by the plug at it back end. The front end may be closed before or after closing of the back end.

Alternatively the plunger is not pre-assembled with the container during filling from the container front end. In this case the container is closed after filling as described for the system not allowing filling from the front end.

BRIEF DESCRIPTION OF THE DRAWINGS

Further advantages will be apparent from the following description and drawings of the preferred embodiments of the present invention.

Figure 1:
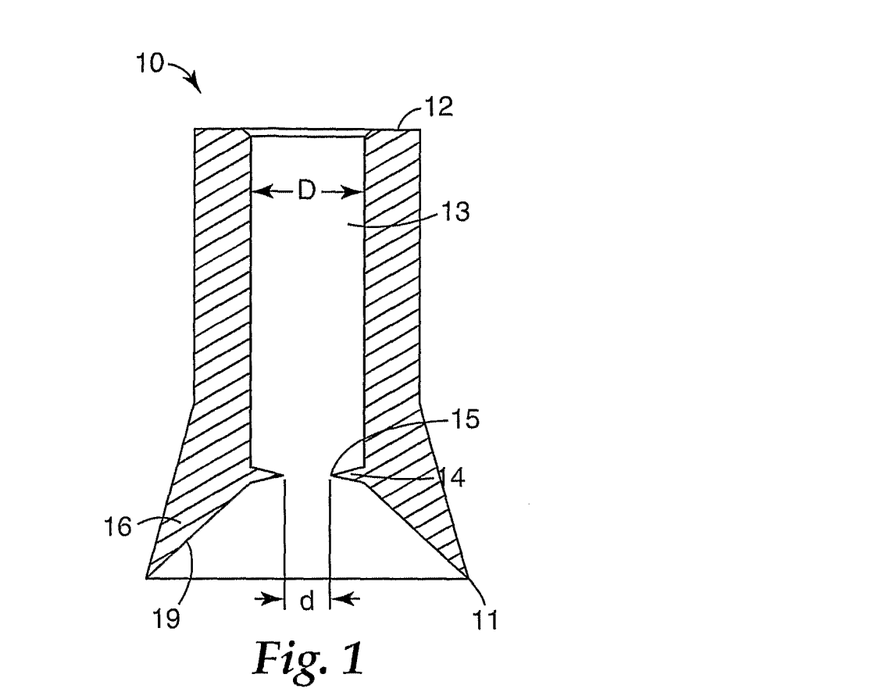
FIG. 1 shows a plunger according to a preferred embodiment of the invention.

FIG. 1 shows a plunger 10 for a cartridge (not shown) according to a first embodiment of the invention. Plunger 10 comprises a first end 11 and an opposite second end 12. Plunger 10 also comprises a passageway 13 that extends between the first end 11 and the second end 12. As shown in FIG. 1, the diameter D of passageway 13 is preferably constant along a substantial length of the passageway 13. Plunger 10 according to the present invention also comprises a constriction 14 that is arranged in the passageway 13 between the first end 11 and the second end 12. Diameter d of the constriction 14 is smaller than diameter D of the passageway 13, and is also smaller than the smallest diameter of a plug (not shown in FIG. 1) that is insertable into the passageway. The plunger-plug combination is described in more detail below.

As shown in FIG. 1, constriction 14 is preferably formed as a sealing lip. In the preferred embodiment shown in FIG. 1, the cross-sectional shape of the sealing lip is substantially triangular. That is, the sealing lip comprises angled surfaces that preferably terminate in an edge 15. Other sealing lips, surfaces, or arrangements may also be used, such as sealing bulges, o-rings, flat sealing collars of a substantially rectangular cross-sectional shape (down to a film-like thickness of e. g. 0.5 mm or less) etc. It may also be provided, that the passageway comprises more than one constriction in a sequential arrangement along its longitudinal axis. Furthermore a combination of various sealing lips, surfaces, or arrangements may be provided.

In the preferred embodiment of FIG. 1, surface 19 at the first end 11 of plunger 10 is angled backwardly towards the passageway 13. In use, plunger 10 is inserted into a cartridge such that surface 19 at the first end 11 of plunger 10 faces the material contained in the cartridge. In the embodiment shown in FIG. 1, the backwardly-angled surface 19 terminates at the constriction 14 so that the backwardly-angled surface 19 and the constriction 14 form an overall surface facing the material that is progressively recessed towards the passageway 13. As will be described in more detail below, air that is present in the container can thus be easily forced into the passageway while the plunger is inserted so that substantially no air is trapped in the container once it is closed by plunger 10 and plug 20.

The first end 11 of plunger 10 is also preferably formed as a second sealing lip 16 for sealing against an outside wall, for example of the container. As shown in FIG. 1, the outer diameter of the plunger 10 increases towards the edge of the plunger 10 at the first end 11.

Figure 2:
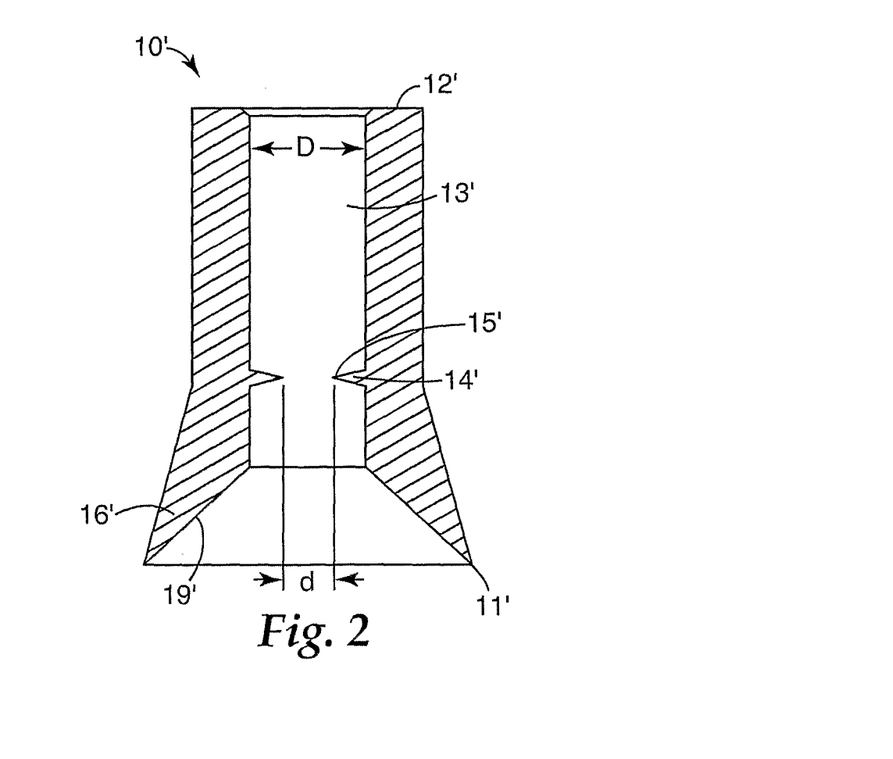
FIG. 2 shows a plunger according to an alternative embodiment of the invention.

FIG. 2 shows an alternative embodiment of the plunger of the invention. Plunger 10' shown in FIG. 2 also comprises a first end 11', an opposite second end 12', and a passageway 13' extending therethrough. However, in contrast to the embodiment shown in FIG. 1, plunger 10' shown in FIG. 2 comprises a constriction 14' that is arranged in the passageway 13' but positioned towards the back end 12' of the passageway 13', i.e. spaced from the area of the plunger 10' where the first end surface 19' of the plunger 10' is angled backwardly towards the passageway 13'.

In the embodiment shown in FIG. 2, the constriction 14' is also formed such that an edge 15' is formed. Moreover, the outer diameter of plunger 10' increases towards the first end 11' so that a second sealing lip 16' is formed.

Figure 3:
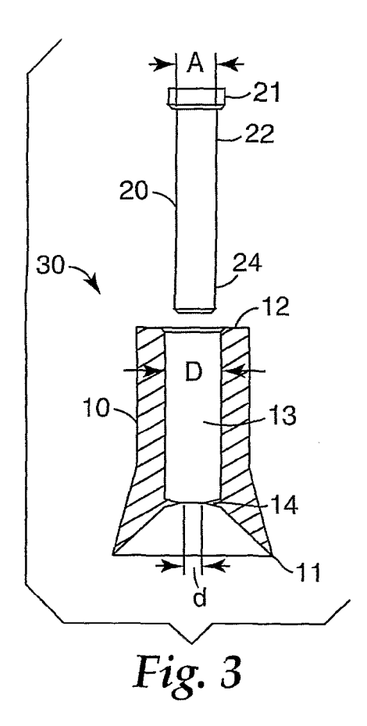
FIG. 3 shows an exploded view of a plunger assembly for a cartridge according to the present invention.

A plunger assembly according to the invention is shown in FIG. 3. FIG. 3 shows plunger assembly 30 comprising a plunger 10 according to the embodiment shown in FIG. 1. However, the plunger assembly 30 is not limited to a plunger 10 according to this embodiment. Other plunger designs such as the embodiment shown in FIG. 2 are also encompassed by the present invention. Plunger assembly 30 also comprises a plug 20. Plug 20 comprises a first end 24 and a second end 22. Preferably, a flange 21 is provided at second end 22. Plunger 10 shown in FIG. 3 is identical to plunger 10 shown in FIG. 1 so that a detailed description of plunger 10 is omitted.

As can be seen in FIG. 3, the diameter d of the constriction 14 is preferably smaller than the diameter A of the plug 20 at least on the area were the constriction 14 seals with the plug 20. The seal between constriction 14 and plug 20 is shown in more detail in FIG. 5. The ratio of the diameter d of the constriction relative to the diameter A of the plug is smaller than 1, preferably within a range of 0.75 to 0.5. In an exemplary embodiment the constriction has a diameter of 1.5 mm and the plug has a diameter of 2.15 mm. These sizes and ratios can depend on the materials from which the various components are made, especially from which the plunger is made. In the exemplary embodiment the plunger is made out of polypropylene. If more rigid materials (e. g. polyamide, polyoxymethylene) are used the ratio d to A will be closer to 1 relative to the exemplary embodiment. Preferably the plugs are made out of polypropylene or of a more rigid material like e.g. polycarbonate, polybutyleneterephtalate, wherein the ratio d to A preferably is similar or equal for the different materials.

It is also preferred in the embodiment shown in FIG. 3 that the diameter D of the passageway 13 is larger than the largest diameter A of the plug 20, in at least one location other than at the constriction 14. The term "largest diameter of the plug" does not include the diameter of a preferred flange 21, as clearly shown in FIG. 3. The ratio of the diameter d of the constriction relative to the diameter D of the passageway is smaller than 1, preferably within a range of 0.75 to 0.5. In an exemplary embodiment the constriction has a diameter of 1.5 mm and the passageway has a diameter of 2.5 mm.

Figure 4:
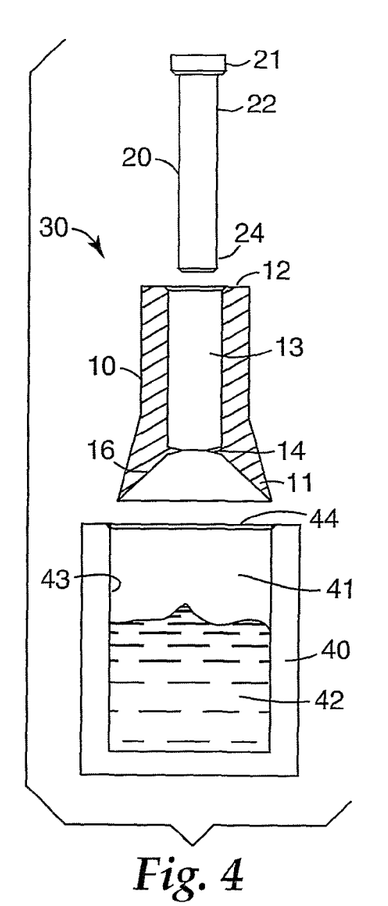
FIG. 4 shows an exploded view of a system for storing a substance according to the present invention.

FIG. 4 shows a system 50 for storing a substance according to the invention. System 50 comprises a container 40, a plunger 10, and a plug 20. Container 40 is a receptacle having a compartment 41 for storing a substance 42. Container 40 furthermore comprises an opening 44 into which plunger 10 can be inserted. Although not shown in FIG. 4, container 40 may also comprise a dispensing opening for dispensing the substance. Preferably, such dispensing opening is located in the container wall opposite opening 44.

Plunger 10 of the invention can be inserted into and moved in the container compartment 41. Once plunger 10 is inserted into the container compartment 41, the second sealing lip 16 of plunger 10 abuts against the inner wall 43 of the container compartment 41 so that a seal is established between second sealing lip 16 and container 40. If no second sealing lip 16 is provided, the outer diameter of plunger 10 preferably corresponds to the compartment diameter so that the plunger wall seals against the compartment wall 43.

Furthermore, plug 20 can be inserted into the passageway 13 of plunger 10, as described in more detail below with reference to FIG. 5.

FIG. 5 shows a sequence of four pictures A through D. In FIG. 5, reference numerals have been essentially omitted in order to clearly show the components of the storing system of the invention. However, since the components of the storing system shown in FIG. 5 are identical to the components shown in FIG. 4, the reference numerals of FIG. 4 will be used for the following explanation of FIG. 5.

Figure 5A:
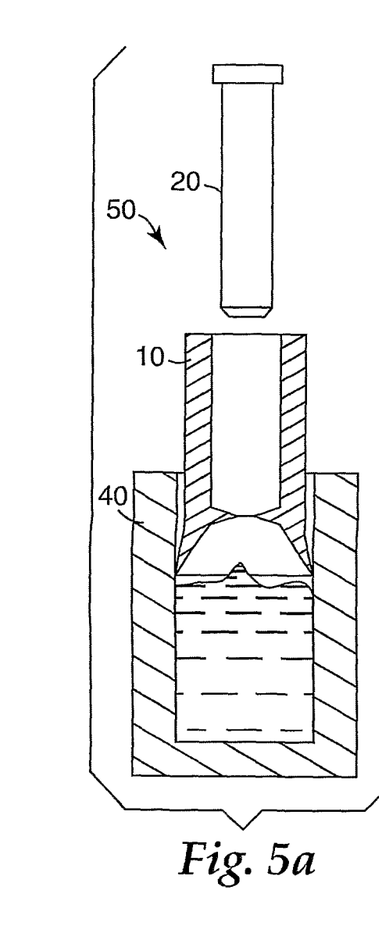
FIGS. 5A, 5B, 5C and 5D show the method of filling and sealing a substance in a storing system (schematic views) according to the inventions.

The components of the storing system of the invention shown in FIG. 5A are identical to the components shown in FIG. 4. However, in contrast to FIG. 4, in FIG. 5A, plunger 10 is already inserted into the container compartment 41 but has not yet reached substance 42.

Figure 5B:
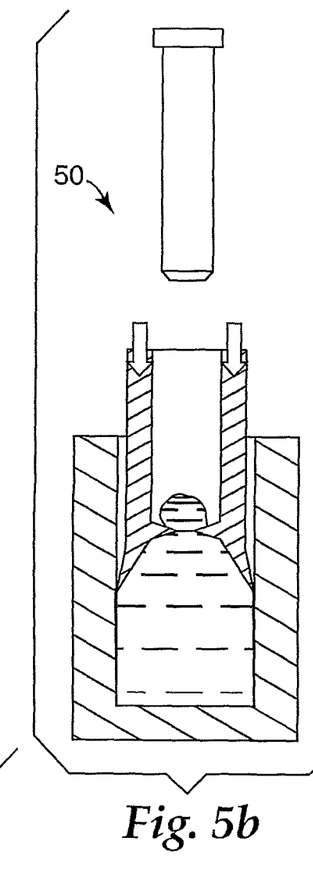

FIG. 5B shows plunger 10 advanced to its desired position within the container compartment 41. The two arrows shown in FIG. 5B indicate that the plunger has been advanced to this position in comparison to FIG. 5A. It can be seen in FIG. 5B that a small amount of the substance 42 stored in the container has been displaced across the constriction 14 into the passageway 13 of the plunger 10.

Figure 5C:
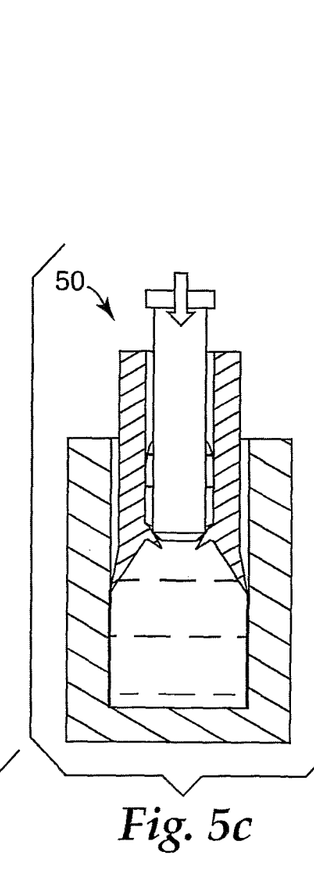

FIG. 5C shows the plug 20 being inserted into the passageway 13 of the plunger 10. The plug 20 has been pushed to a position where its front end 24 already contacts the sealing lip 14. FIG. 5C clearly shows that sealing lip 14 is already slightly deflected by the plug 20 towards the interior of the container.

It is also shown in FIG. 5C that the diameter A of the plug 20 is smaller than the diameter D of the passageway 13 of the plunger 10 so that a space 17 (see FIG. 5D) is formed between the wall of the passageway 13 and plug 20. Excess material is stored in space 17.

Figure 5D:
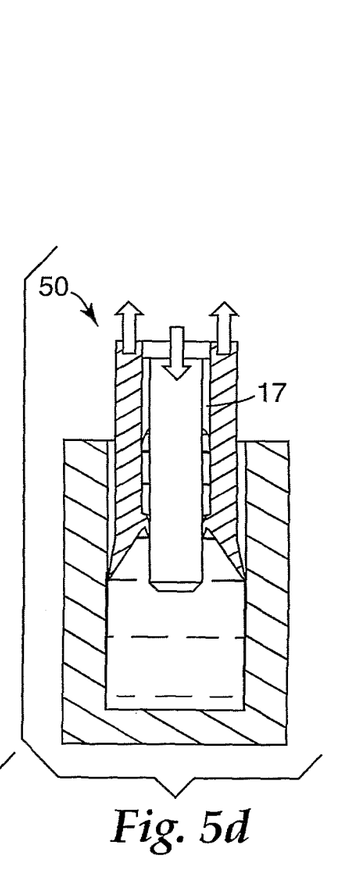

In FIG. 5C, the compartment is fully closed by the plunger 10 and plug 20. Upon further movement of the plug 20 into the plunger 10, the plunger 10 is pushed back, which is shown in FIG. 5D by the two black arrows pointing upwards. Plunger 10 is pushed back by the pressure which builds up within the material stored in the container 40 because the material 42 is substantially incompressible. If the plug 20 comprises a flange 21 at its back end 22, the plug 20 is preferably pushed into the plunger 10 until the second end 12 of the plunger 10 has reached the flange 21 of the plug 20 so that the upper end of the space 17 between the plug 20 and the plunger 10 is closed by the flange 21 (see FIG. 5D). Excess substance is thus kept in the space 17.

Although not shown, it is preferred that the plug 20 is pushed completely into the plunger 10 and moved back by a short distance in order to relieve residual pressure. This residual pressure results from a certain elasticity of the container walls and from the fact that a balance will be reached between the pressure building up in the container and friction forces that have to be overcome to move plug 20 relative to seal 14 as well as to push plunger 10 back within the container.

Figure 8:
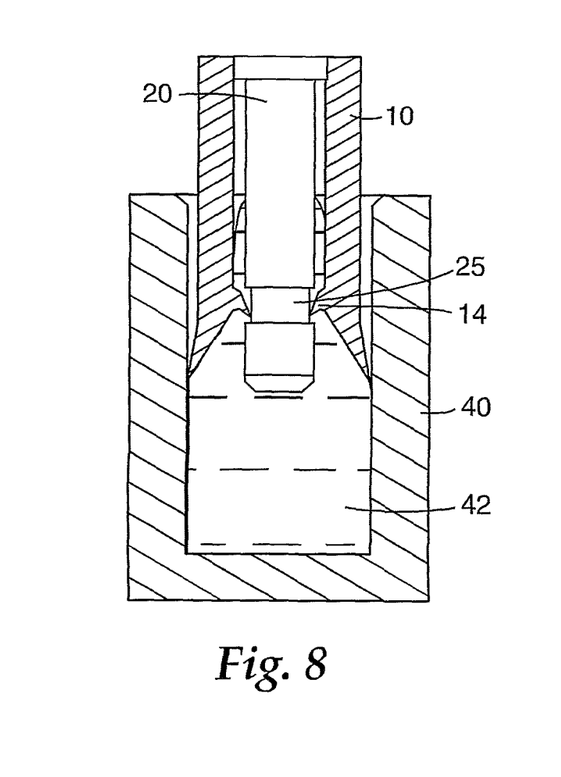
FIG. 8 shows the system of FIG. 4 with a modified plug.

As shown in FIG. 8, the plug 20 preferably comprises a stepped configuration or indented ring 25 with a smaller diameter into which the constriction lip 14 fits to lock the plug 20 in place within the plunger 10.

It is also clear from FIG. 5 that air that is present in the space between the first end surface 19 of the plunger 10, and the substance 42 contained in the container 40 is allowed to escape through the constriction 14 and through the vent passageway 13. Due to the backwardly-angled shape of the surface 19 of the plunger 10, and due to the angled surface of the constriction 14, any air is forced upwards to the vent passageway so that almost no air is trapped in the container when excess material flows into the passageway (see FIG. 5B). Initially, the plunger does not have structures allowing air to be trapped when the plunger is pushed into the substance because the sealing lip is undeflected. However, the sealing lip forms an improved seal after the plug is inserted. The material in the container is completely sealed due to the seal between sealing lip 14 and plug 20, and due to the seal between second sealing lip 16 and the container wall.

Since the sealing lip 14 is oriented towards the material (see FIG. 5D), the sealing effect will even increase when the pressure in the material increases, for example, when material is pressed forward by the plunger and plug and dispensed through a dispensing opening (not shown). The taper providing the second sealing lip also increases the seal effect when the pressure on the lip increases. An additional seal effect as well as a lock of the plug in the plunger are provided by the indented ring 25 (see FIG. 8). Due to the step in diameter, the plug is locked against the constriction 14 so that continued pressure of the plunger 10 forward does not cause the substance to force the plug backward and out of sealing engagement with the constriction 14.

Figure 6:
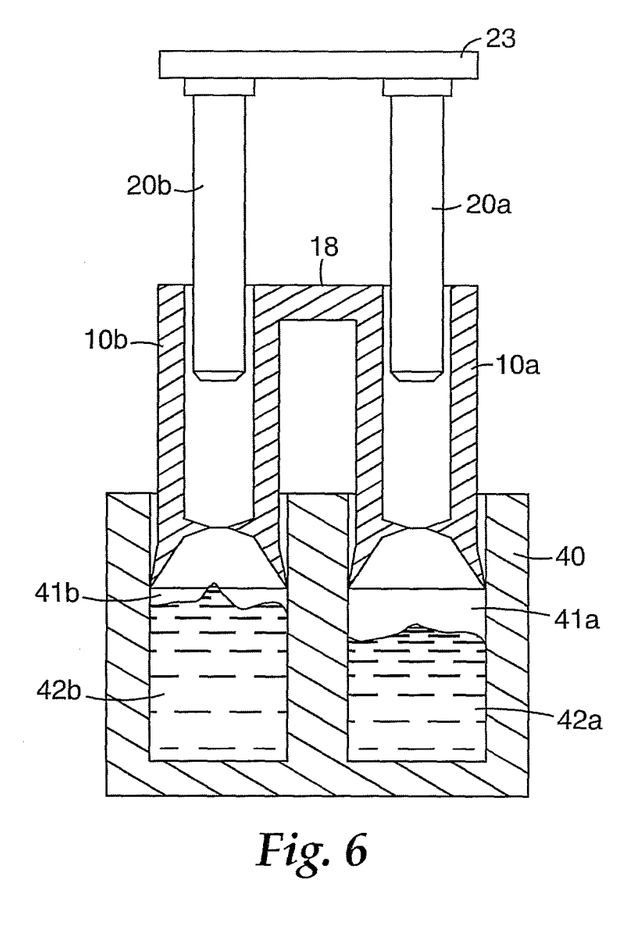
FIG. 6 shows a system for storing a substance according to an alternative embodiment of the invention.

FIG. 6 shows an alternative embodiment of the storing system of the invention. In the embodiments shown in FIG. 6, the container 40 comprises a first compartment 41a for a first substance 42a, and a second compartment 41b for a second substance 42b. A first plunger 10a is provided for the first compartment 41a, and a second plunger 10b is provided for the second compartment 41b. In the preferred embodiment shown in FIG. 6, the two plungers 10a and 10b are connected to each other by a connecting bar 18. Preferably, the two plungers 10a and 10b are integrally formed as one piece.

Figure 9:
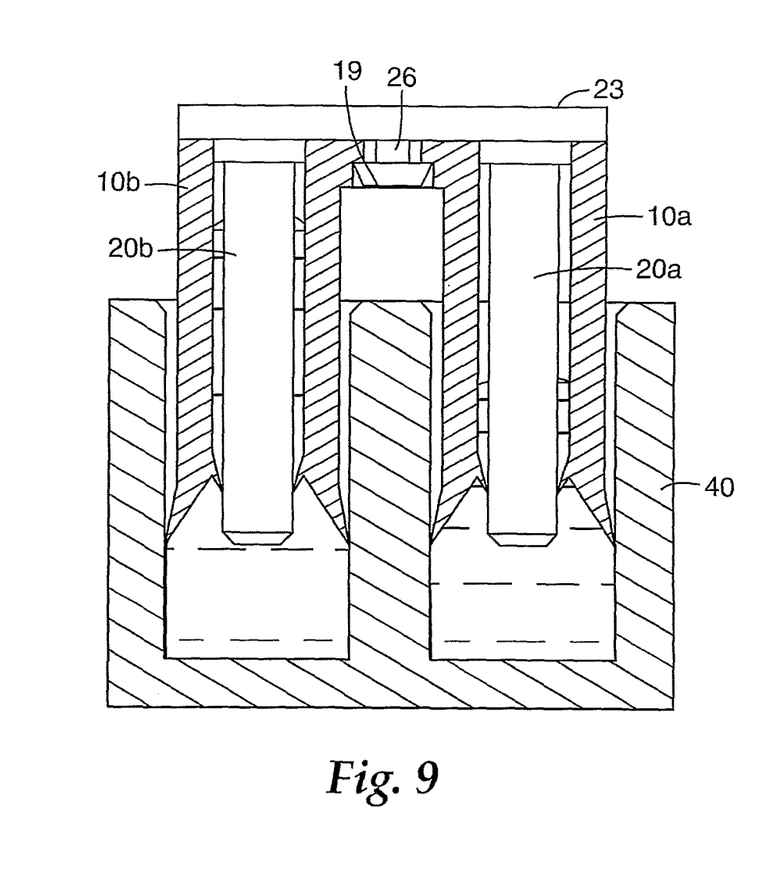
FIG. 9 shows the system of FIG. 6 with an additional retention element.

A first plug 20a and a second plug 20b are provided for sealing the compartments. The two plugs 20a and 20b are preferably connected by a connecting bar 23. Preferably, a retention element 26 (shown in FIG. 9) is provided at the connecting bar 23. Retention element 26 engages with a corresponding recess 19 at the back end of the walls of plungers 10a, 10b. Once engagement is established, the relative position between plugs 20a, 20b and plungers 10a, 10b is substantially fixed.

FIG. 7 shows how two different substances can be sealed in the two compartments of the storing system of FIG. 6. Since the components shown in the four pictures of FIG. 7 are identical to the components shown in FIG. 6, reference numerals are omitted in FIG. 7 for clarity.

Figure 7A:
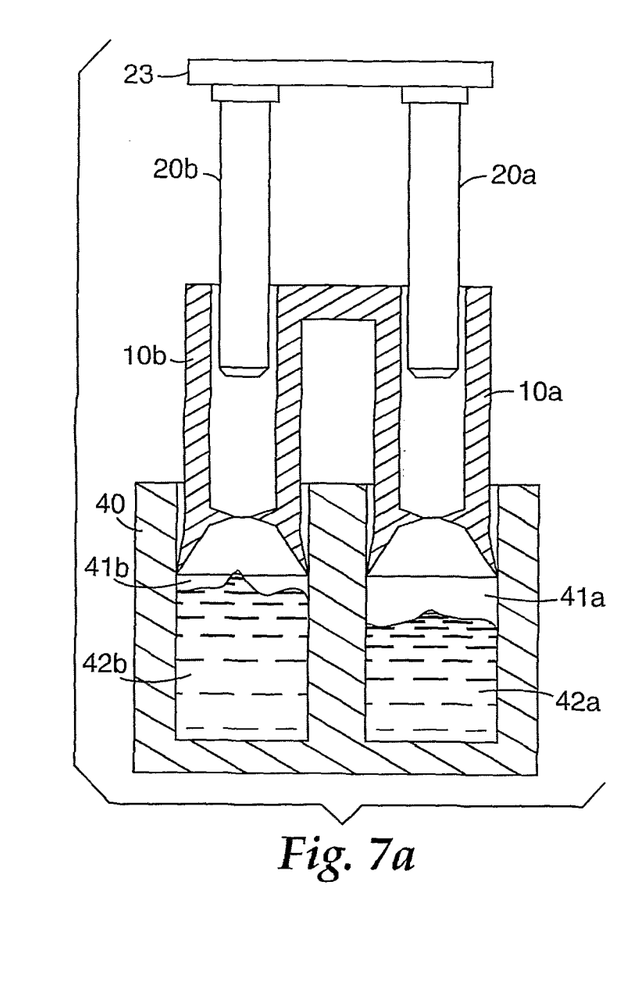
FIGS. 7A, 7B, 7C and 7D show the method of filling and sealing a substance in a storing system (schematic views) according to FIG. 6

FIG. 7A shows the components of the storing system of this embodiment of the invention in their initial position. FIG. 7A is identical to FIG. 6. As can be seen in FIG. 7A, the two compartments are filled with the substances to different fill levels.

Figure 7B:
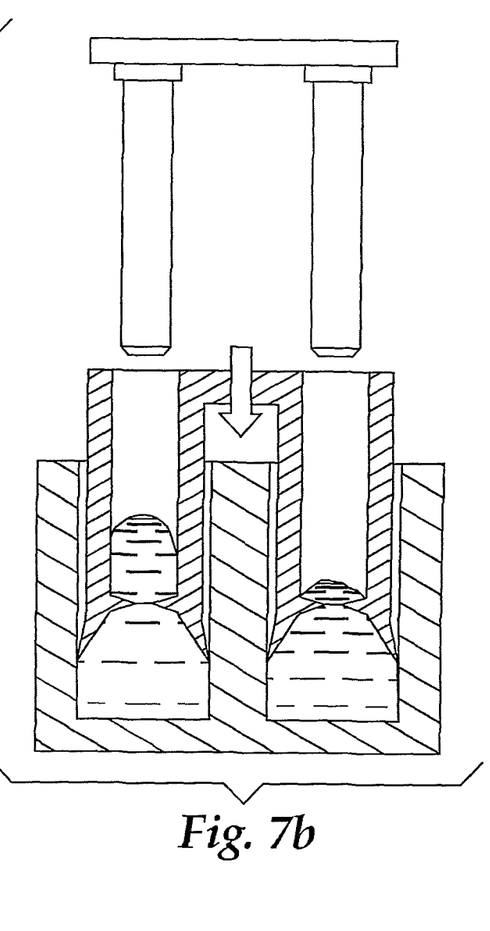
Figure 7C:
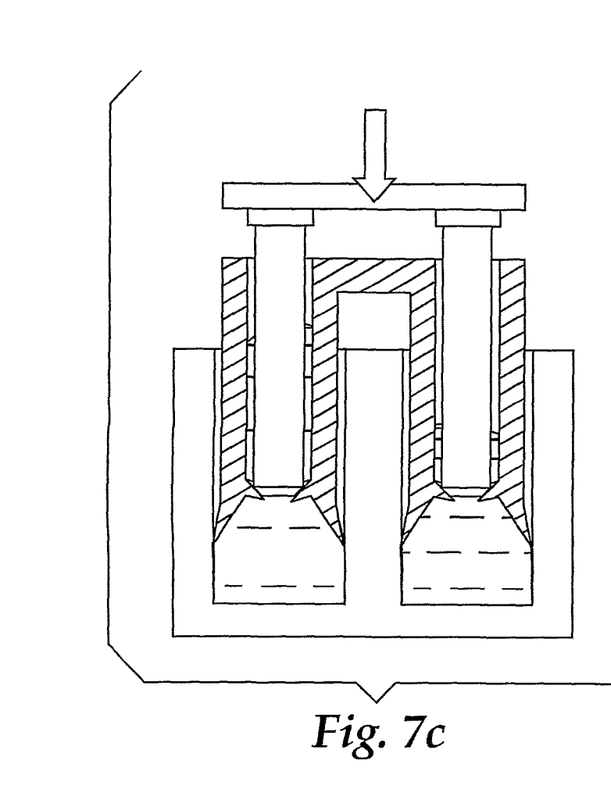

In FIG. 7B, the plungers have already been advanced to their desired position. Due to the different fill levels in the different compartments, different amounts of excess substance have passed the constriction and are now contained in the passageway of each plunger. In the next step, the two plugs are inserted into the passageways until they reach and deflect the sealing lips to form a seal (FIG. 7C). The excess substance contained in the passageway of each plunger is stored in the space between the plug and the plunger wall. In the final step (see FIG. 7D), the plungers are pushed further into the compartments so that the substantially incompressible material lifts the plungers until the connecting bar of the plunger contacts the connection bar of the plugs.

Although not shown, it is preferred that the plugs are pushed completely into the plungers and then moved back by a short distance in order to relieve residual pressure. This residual pressure results from a certain elasticity of the container walls and from the fact that a balance will be reached between the pressure building up in the container and friction forces that have to be overcome to move plugs relative to seals as well as to push the plungers back within the container compartments.

The embodiment of the storing system shown in FIGS. 6 and 7 is advantageous because it compensates for imprecise fill tolerances and different fill levels in the container compartments. This is beneficial because it is very difficult to fill two compartments with precisely equal amounts or equal fill levels of material.

This is especially advantageous if the invention is used in combination with a delivery system having two or more compartments filled with components that are mixed together when the system is used (e. g. when the substances stored in the compartments are expelled through a single dispensing opening by displacing the plunger assembly). In this case the filling volumes of the individual components have to be within a predefined ratio relative to each other (e. g. 1:1, 2:1, 3:1 etc).

Figure 7D:
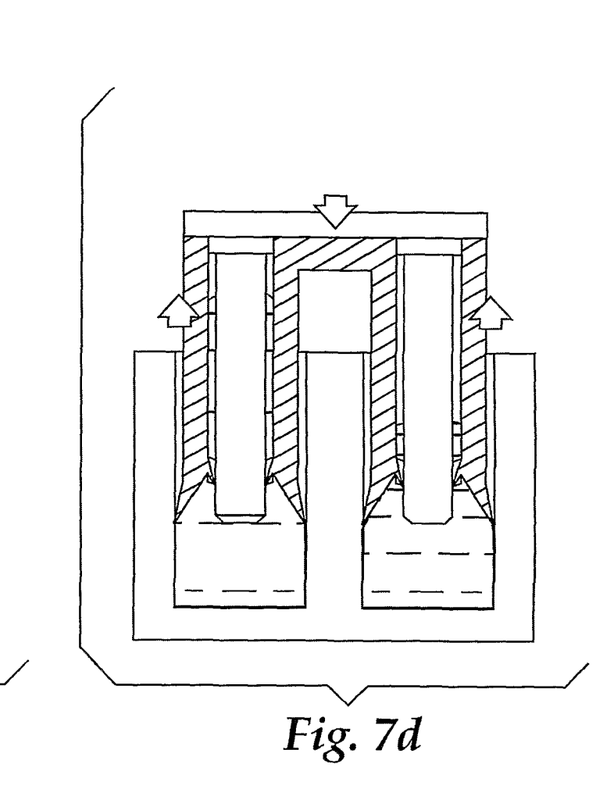

If a dual plunger arrangement is used (as in FIGS. 6 and 7), the plungers are simultaneously advanced towards the substance until both compartments are substantially free of air (in the manner described above, and also as shown in FIG. 7B). The dual plug arrangement is pushed into the passageways of the plunger arrangement, thus sealing the compartment (FIGS. 7C and 7D). As it can be seen in FIG. 7D, the ratio of the filling volume of the individual components is defined by the geometry of the delivery system rather than the filling system.

In an alternative embodiment to the storing system shown in FIGS. 6 and 7 the plungers are of a different length, different diameters, or the plungers (not connected to each other) are inserted to different positions within the compartment. This is advantageous if the storing system is used for providing components in unequal proportion for mixing after the components have been completely expelled from the delivery system. Thus, the invention includes a system having materials in two compartments wherein there are substantially different amounts of material in the two compartments, for example ratios of from approximately 1:2 to approximately 1:10.

Figure 10:
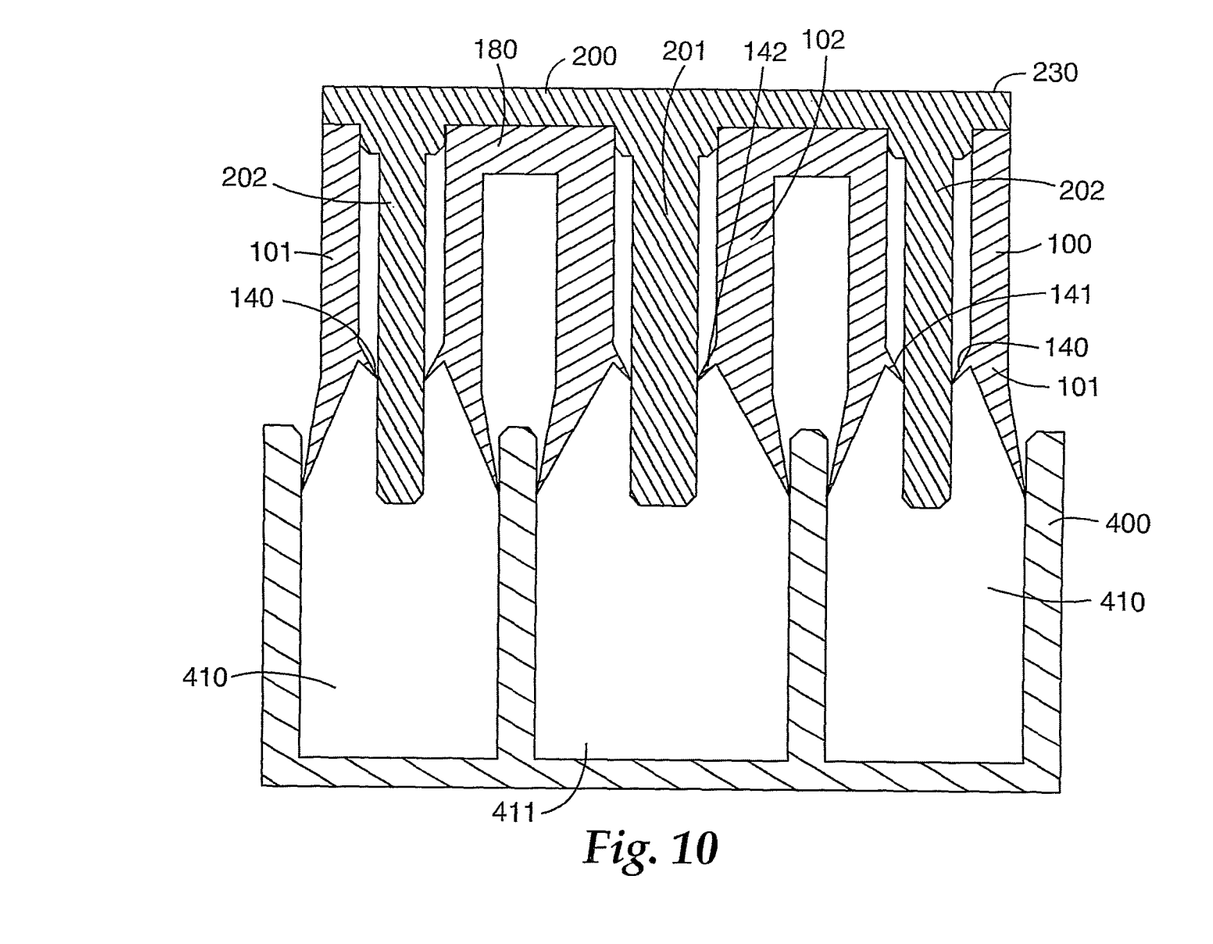
FIG. 10 shows a system for storing a substance according to a further alternative embodiment of the invention.

FIG. 10 shows a system for storing a substance according to a further alternative embodiment of the invention. The system of the embodiment of FIG. 10 also comprises two compartments for storing two materials. In this embodiment, these two compartments are arranged concentrically within container 400. Reference numeral 411 denotes the inner compartment which is surrounded by annular compartment 410.

In the same way, plunger 100 comprises an inner plunger portion 102 as well as an annular outer plunger portion 101. Both plunger portions 101, 102 are arranged concentrically. Outer plunger portion 101 is substantially cylindrical and comprises at its inner surface a sealing lip 140. The inner plunger portion 102 is substantially inverse U-shaped and substantially annular. At its outer surface, a sealing lip 141 is provided. Sealing lips 140 and 141 from a first constriction associated with the outer compartment 410. The inner surface of annular plunger portion 102 comprises a constriction 142 associated with the inner compartment 411. Apart from the concentric arrangement, plunger 100 and the provided constrictions are arranged and dimensioned as described above with reference to the other embodiments of the present invention.

Plug 200 comprises an inner plug portion 201 and an outer annular plug portion 202. Both plug portions 201, 202 are concentrically arranged. The annular outer plug portion 202 and the inner cylindrical plug portion 201 are connected by connecting plate or disk 230. As shown in FIG. 10, the constrictions of the plunger seal against the plug portions extending through the plunger passageways.

Plunger 100 is preferably integrally formed as one part, wherein the plunger portions 101, 102 are connected preferably by spokes at their back end. In the area of the spokes of plunger 100 the connecting disk 230 of plug 200 is recessed so that both parts engage with one another when assembled with each other (not shown).

Figure 11:
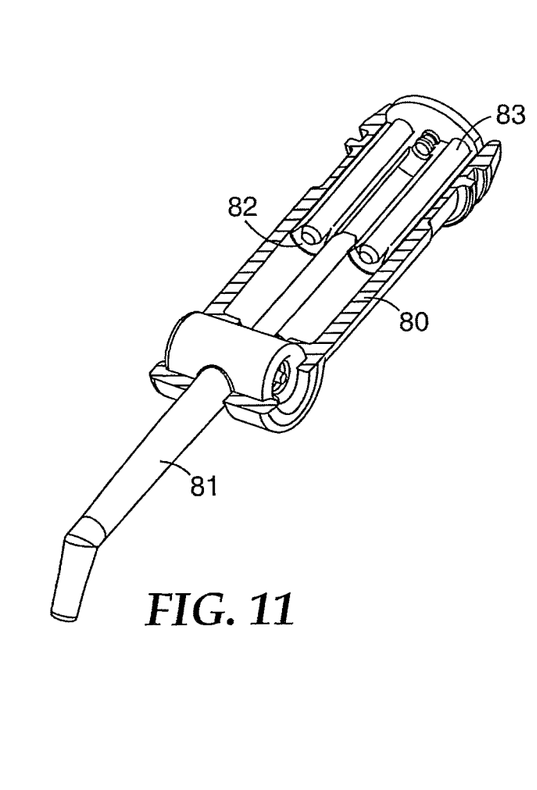
FIG. 11 shows a cross-sectional view of a container having two compartments and a dispensing cannula.
Figure 12:
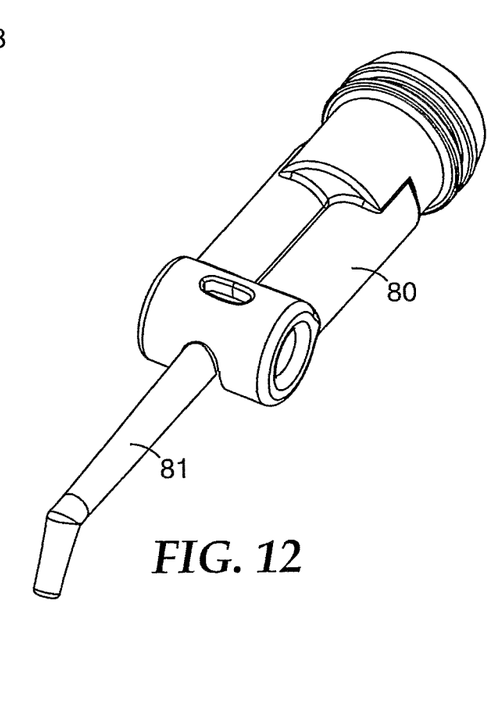
FIG. 12 shows a perspective view of the container of FIG. 11.

An exemplary container 80 having two compartments and a dispensing cannula 81 is shown in FIGS. 11 and 12. The plunger 82 and plug 83 assembly according to the present invention is also shown in these Figs. Similar containers for use with the system of the present invention are shown in WO 2005/016783.

Figure 13A:
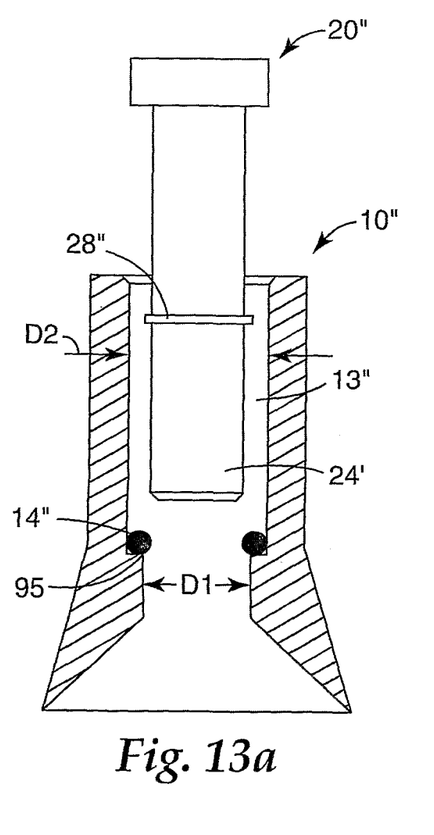
FIG. 13a, b show a plunger assembly for a cartridge according to a further embodiment of the invention.
Figure 13B:
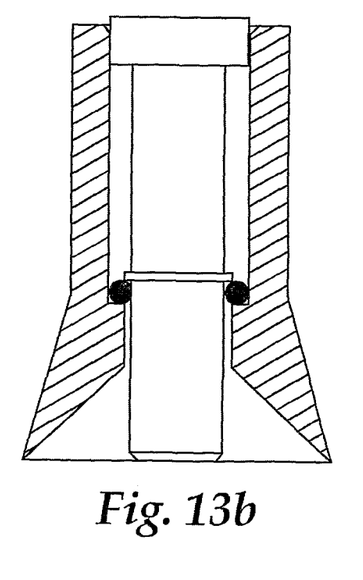

FIGS. 13a and 13b show a plunger assembly according to a further embodiment of the present invention. A seal 14" is provided as separate part and assembled into the passageway 13" of the plunger 10". Seal 14" preferably has a triangular cross-sectional shape (not shown) or a circular cross-sectional shape (o-ring). The passageway 13" of this embodiment preferably (but not necessarily) has a stepped configuration, which means that the passageway has a first diameter D1 towards the front end of the plunger 10" and a second diameter D2 towards the back end of the plunger 10", wherein the first diameter D1 is smaller then the second diameter D2. The seal 14" is received in the second diameter D2 and abuts at the step 95 between the first and second diameter D1, D2, thus being fixed against displacement when the plug 20" is inserted in the passageway 13".

In FIG. 13a the plug 20" is still not completely inserted into the passageway 13" of the plunger 10". FIG. 13b shows the plunger assembly of this embodiment of the invention after the plug 20" has been inserted in the passageway 13". In this stage the plug 20" seals with the plunger 10" by compressing the seal 14" between the wall of the passageway with the diameter D2 and the plug 24'. Preferably, plug 20" comprises a circumferential flange 28" for pressing the seal against the step 95.

Figure 14A:
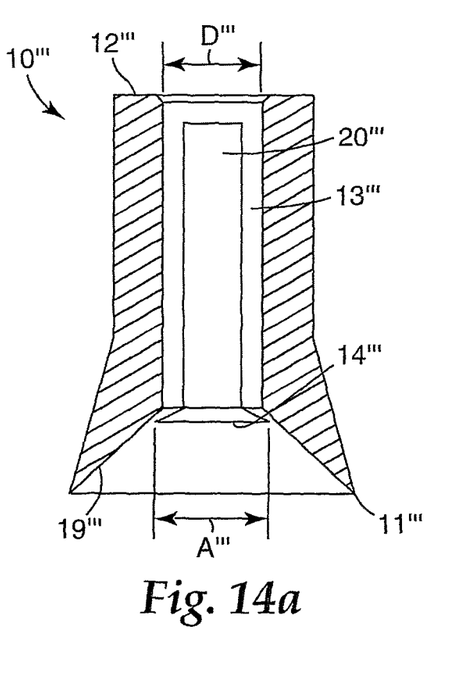
FIG. 14a, b show a plunger assembly for a cartridge according to a further embodiment of the invention.
Figure 14B:
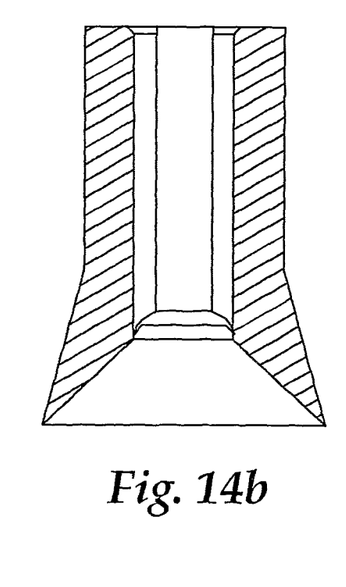

FIGS. 14a and 14b show a plunger assembly according to a further embodiment of the invention. A seal 14''' is provided at the front end of the plug 20'''. The seal 14''' is preferably of a triangular cross-sectional shape and preferably deformable, thus forming a flexible sealing lip. Preferably the diameter A''' of the sealing lip 14''' is substantially larger than the diameter D''' of the passageway 13'''. The plug 20''' is preferably pre-assembled with the plunger 10''' in a manner that the back end of the plug 20''' is located in the passageway 13''' of the plunger 10''' and the sealing lip 14''' is located outside of the passageway 13'''. Preferably the sealing lip 14''' is located within the inwardly tapered area 19''' at the front end of the plunger 10''', wherein the sealing lip 14''' does not touch the plunger 10''', providing that the plug 20''' does not seal with the plunger 10''' at this stage (shown in FIG. 14a).

FIG. 14b shows the plunger assembly according to this embodiment of the invention in a stage where the plug 20''' has been pulled back towards the back end of the plunger 10''', and the sealing lip 14''' has moved into the passageway 13'''. In this stage the plug 20''' seals with the plunger 10'''. Because of the larger diameter A''' of the sealing lip 14''' and since the sealing lip is deformable, the sealing lip 14''' has deflected towards a direction of the front end of the plunger 11''' upon displacement into the passageway.

The present invention has now been described with reference to several embodiments thereof. The foregoing detailed description has been given for clarity of understanding only. No unnecessary limitations are to be understood therefrom. Many changes can be made in the embodiments described without departing from the scope of the invention.

Thus, the scope of the present invention should not be limited to the exact details and structures described herein, but rather by the structures described by the language of the claims and the equivalents of those structures.

The invention claimed is:

1. A system comprising:
   a cartridge comprising a first compartment and a second compartment;
   a first plunger at least partially inserted into the first compartment, wherein the first plunger has a first end and an opposite second end, wherein an outer diameter of the first plunger increases towards an edge of the first plunger at the first end such that the outer diameter is configured to form a first seal with an inner wall of the first compartment, and the first plunger having a passageway extending between the first and second ends, wherein the passageway comprises a sealing lip projecting into the passageway;
   a second plunger at least partially inserted into the second compartment, wherein the second plunger has a first end and an opposite second end, wherein an outer diameter of the second plunger increases towards an edge of the second plunger at the first end such that the outer diameter is configured to form a first seal with an inner wall of the second compartment, and the second plunger having a passageway extending between the first and second ends, wherein the passageway comprises a sealing lip projecting into the passageway;
   a first connecting bar that connects the first plunger and the second plunger at the second end of the first plunger and the second plunger;
   a first plug having a first end and a second end, wherein the first plug is configured for insertion into the passageway of the first plunger to close the passageway at the sealing lip by combining with the sealing lip to form a second seal at the sealing lip;
   a second plug having a first end and a second end, wherein the second plug is configured for insertion into the passageway of the second plunger to close the passageway at the sealing lip by combining with the sealing lip to form a second seal at the sealing lip; and
   a second connecting bar that connects the first plug and the second plug at the second end of the first plug and the second plug.

2. The system of claim 1, wherein the surface of each sealing lip is angled towards the passageway into which each sealing lip extends.

3. The system of claim 1, wherein each sealing lip is elastic.

4. The system of claim 1,
   wherein the sealing lip of each of the first plunger and the second plunger is a first sealing lip,
   wherein the first end edge of each plunger is provided as a second sealing lip.

5. A plunger assembly for a cartridge comprising a first compartment and a second compartment, the plunger assembly comprising:
   a first plunger having a first end and an opposite second end, and comprising a passageway extending between the first and second ends, wherein the passageway comprises a deformable first sealing lip projecting into the passageway and wherein the first end edge of the first plunger provides a second sealing lip, wherein the second sealing lip is configured to form a seal with an inner wall of the first compartment;
   a second plunger having a first end and an opposite second end, and comprising a passageway extending between the first and second ends, wherein the passageway comprises a deformable first sealing lip projecting into the passageway and wherein the first end edge of the second plunger provides a second sealing lip, wherein the second sealing lip is configured to form a seal with an inner wall of the second compartment,
   a first connecting bar that connects the first plunger and the second plunger at the second end of the first plunger and the second plunger;
   a first plug having a first end and a second end, wherein the first plug is insertable into the passageway of the first plunger, wherein the first plug is configured close the passageway at the first sealing lip of the first plunger;
   a second plug having a first end and a second end, wherein the second plug is insertable into the passageway of the second plunger, wherein the second plug is configured close the passageway at the first sealing lip of the second plunger; and
   a second connecting bar that connects the first plug and the second plug at the second end of the first plug and the second plug.

6. The plunger assembly of claim 5, wherein the first plunger and the second plunger each comprise a surface at the first end, each surface being backwardly-angled towards the passageway of each respective first plunger and second plunger.

7. The plunger assembly of claim 6, wherein the backwardly-angled surface terminates in the deformable first sealing lip.

8. The plunger assembly of claim 5, wherein the first connecting bar and the second connecting bar are in physical contact with each other.

9. The plunger assembly of claim 5, wherein the first connecting bar includes a recess and the second connecting bar includes a retention element that engages with the recess to substantially fix a position between the first plug, the second plug, the first plunger and the second plunger.

10. The system of claim 1, wherein the first connecting bar and the second connecting are in physical contact with each other.

11. The system of claim 1, wherein the first connecting bar includes a recess and the second connecting bar includes a retention element that engages with the recess to substantially fix a position between the first plug, the second plug, the first plunger and the second plunger.

12. The system of claim 1, wherein the first compartment includes a first substance and the second compartment includes a second substance different than the first substance, and wherein only the first substance simultaneously contacts both the first seal of the first plunger and the second seal at the sealing lip of the first plug and only the second substance simultaneously contacts both the first seal of the second plunger and the second seal at the sealing lip of the second plug.

13. The system of claim 12, wherein the first substance is present in the passageway on either side of the sealing lip of the first plunger and the second substance is present in the passageway on either side of the sealing lip of the second plunger.

* * * * *

UNITED STATES PATENT AND TRADEMARK OFFICE
CERTIFICATE OF CORRECTION

PATENT NO. : 9,844,796 B2
APPLICATION NO. : 12/089920
DATED : December 19, 2017
INVENTOR(S) : Arno Hohmann It is certified that error appears in the above-identified patent and that said Letters Patent is hereby corrected as shown below:

In the Specification

Column 5
Line 7, delete "then" and insert -- than --, therefor.
Lines 18-26, delete "Preferably the diameter of the sealing lip is substantially larger than the diameter of the passageway. The plug is preferably pre-assembled with the plunger in a manner that the back end of the plug is located in the passageway of the plunger and the sealing lip is located outside of the passageway. Preferably the sealing lip is located within the inwardly tapered area at the front end of the plunger, wherein the sealing lip does not touch the plunger, providing that the plug does not seal with the plunger at this stage." and insert the same in Column 5, Line 17, as a continuation of the same paragraph.

Column 6
Line 56, delete "FIG. 6" and insert -- FIG. 6; --, therefor.

Column 8
Lines 26-27, delete "polybutyleneterephtalate," and insert -- polybutyleneterephthalate, --, therefor.

Column 12
Line 23, delete "then" and insert -- than --, therefor.

In the Claims

Column 14
Lines 14-15, in Claim 5, after "close" insert -- to --.
Lines 19-20, in Claim 5, after "close" insert -- to --.
Line 44 (approx.), in Claim 10, after "connecting" insert -- bar --.

Signed and Sealed this
Tenth Day of July, 2018

Andrei Iancu
*Director of the United States Patent and Trademark Office*